US00PP18677P2

(12) United States Plant Patent
Verheijen

(10) Patent No.: US PP18,677 P2
(45) Date of Patent: Apr. 1, 2008

(54) ***HYPERICUM* PLANT NAMED 'VERPEACLA'**

(50) Latin Name: *Hypericum androsaemum*
Varietal Denomination: Verpeacla

(75) Inventor: Edwin Martijn Verheijen, Wieringerwerf (NL)

(73) Assignee: Handelskwerkerij Verheijen vof, Wieringerwerf (NL)

( * ) Notice: Subject to any disclaimer, the term of this patent is extended or adjusted under 35 U.S.C. 154(b) by 0 days.

(21) Appl. No.: 11/637,851

(22) Filed: Dec. 12, 2006

(51) Int. Cl.
*A01H 5/00* (2006.01)

(52) U.S. Cl. ..... Plt./226

(58) Field of Classification Search ..... Plt./226, Plt./263

See application file for complete search history.

*Primary Examiner*—Kent Bell
(74) *Attorney, Agent, or Firm*—C. A. Whealy

(57) ABSTRACT

A new and distinct cultivar of *Hypericum* plant named 'Verpeacla', characterized by its upright plant habit; durable dark green-colored leaves; freely flowering habit; large light pink-colored fruits; and good postproduction longevity.

2 Drawing Sheets

Botanical designation: *Hypericum androsaemum.*
Cultivar denomination: 'Verpeacla'.

BACKGROUND OF THE INVENTION

The present invention relates to a new and distinct cultivar of *Hypericum,* botanically known as *Hypericum androsaemum* and hereinafter referred to by the name 'Verpeacla'.

The new *Hypericum* is a product of a planned breeding program conducted by the Inventor in Wieringerwerf, The Netherlands. The objective of the breeding program is to create new cut flower *Hypericum* cultivars with numerous attractive fruit coloration.

The new *Hypericum* originated from a cross-pollination made by the Inventor in August, 2001 in Wieringerwerf, The Netherlands of a proprietary selection of *Hypericum androsaemum* identified as code number 22-22-53, not patented, as the female, or seed parent with a proprietary selection of *Hypericum androsaemum* identified as code number 1062, not patented, as the male, or pollen, parent. The new *Hypericum* was discovered and selected by the Inventor as a single flowering plant within the progeny of the stated cross-pollination in a controlled environment in Wieringerwerf, The Netherlands in July, 2003.

Asexual reproduction of the new cultivar by vegetative cuttings in Wieringerwerf, The Netherlands, since August, 2003, has shown that the unique features of this new *Hypericum* are stable and reproduced true to type in successive generations.

SUMMARY OF THE INVENTION

Plants of the cultivar Verpeacla have not been observed under all possible environmental conditions. The phenotype may vary somewhat with variations in environment such as temperature and light intensity without, however, any variance in genotype.

The following traits have been repeatedly observed and are determined to be the unique characteristics of 'Verpeacla'. These characteristics in combination distinguish 'Verpeacla' as a new and distinct cultivar of *Hypericum:*

1. Upright plant habit.
2. Durable dark green-colored leaves.

3. Freely flowering habit.
4. Large light pink-colored fruits.
5. Good postproduction longevity.

Plants of the new *Hypericum* differ from plants of the female parent selection in the following characteristics:

1. Plants of the new *Hypericum* have larger inflorescences than plants of the female parent selection.
2. Plants of the new *Hypericum* have larger fruits than plants of the female parent selection.
3. Plants of the new *Hypericum* differ from plants of the female parent selection in fruit color as plants of the female parent selection have brownish red-colored fruits.

Plants of the new *Hypericum* differ from plants of the male parent selection in the following characteristics:

1. Plants of the new *Hypericum* have longer flowering stems than plants of the male parent selection.
2. Plants of the new *Hypericum* have larger fruits than plants of the male parent selection.

Plants of the new *Hypericum* can be compared to plants of the cultivar Excellent Flair, not patented. In side-by-side comparisons conducted by the Inventor in Wieringerwerf, The Netherlands, plants of the new *Hypericum* differed from plants of the cultivar Excellent Flair in the following characteristics:

1. Plants of the new *Hypericum* were more upright and shorter than plants of the cultivar Excellent Flair.
2. Plants of the new *Hypericum* were more freely branching than plants of the cultivar Excellent Flair.
3. Plants of the new *Hypericum* had stronger flowering stems than plants of the cultivar Excellent Flair.
4. Leaves of plants of the new *Hypericum* were larger, had more rounded apices and were darker green in color than leaves of plants of the cultivar Excellent Flair.
5. Plants of the new *Hypericum* and the cultivar Excellent Flair differed in fruit color as plants of the cultivar Excellent Flair had brownish red-colored fruits.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Hypericum*.

The photograph on the first sheet comprises a side perspective view of a typical flowering stem of 'Verpeacla'.

The photograph at the top of the second sheet is a close-up view of typical fruits of 'Verpeacla'.

The photograph at the bottom of the second sheet is a close-up view of a typical flower of 'Verpeacla'.

DETAILED BOTANICAL DESCRIPTION

In the following description, color references are made to The Royal Horticultural Society Colour Chart, 1995 Edition, except where general terms of ordinary dictionary significance are used. Plants used for the aforementioned photographs and following description were grown under conditions which closely approximate commercial production conditions during the summer in an outdoor nursery in Wieringerwerf, The Netherlands for about one year. During the production of the plants, day temperatures ranged from 14° C. to 30° C. and night temperatures ranged from 10° C. to averaged 14° C.

Botanical classification: *Hypericum androsaemum* cultivar Verpeacla.

Parentage:

*Female, or seed, parent.*—Proprietary selection of *Hypericum androsaemum* identified as code number 22-22-53, not patented.

*Male, or pollen, parent.*—Proprietary selection of *Hypericum androsaemum* identified as code number 1062, not patented.

Propagation:

*Type cutting.*—Vegetative cuttings.

*Time to initiate roots, summer.*—About twelve days at 21° C.

*Time to initiate roots, winter.*—About three weeks at 21° C.

*Time to produce a rooted young plant, summer.*—About one month at 21° C.

*Time to produce a rooted young plant, winter.*—About 40 days at 21° C.

*Root description.*—Fine, fibrous; color, 163A overlain with 200A.

*Rooting habit.*—Freely branching; dense.

Plant description:

*Form.*—Upright plant form; narrow inverted triangle. Freely branching with about ten flowering stems developing per plant; dense and bushy plant form; moderately vigorous growth habit.

*Plant height.*—About 65 cm.

*Plant width (spread).*—About 70 cm.

*Lateral branch description.*—Length: About 12 cm. Diameter: About 2.7 mm. Internode length: About 3.5 cm. Strength: Strong. Texture: Smooth, glabrous. Color, young: 145C overlain with 53A. Color, mature: 165B.

Foliage description:

*Arrangement.*—Opposite, simple; sessile.

*Length.*—About 7.2 cm.

*Width.*—About 5.4 cm.

*Shape.*—Ovate.

*Apex.*—Rounded and slightly retuse.

*Base.*—Slightly cordate.

*Margin.*—Entire; slightly undulate.

*Texture, upper and lower surfaces.*—Glabrous; rugose.

*Venation pattern.*—Pinnate.

*Color.*—Developing foliage, upper surface: Close to 144A. Developing foliage, lower surface: Close to 138D. Fully expanded foliage, upper surface: Darker than 139A; venation, close to 147D. Fully expanded foliage, lower surface: 139C; venation, 147D.

*Stipules.*—Length: About 5 mm. Width: About 3.5 mm. Texture, upper and lower surfaces: Glabrous; slightly rugose. Color, upper surface: 143A. Color, lower surface: 138B.

Flower description:

*Flower arrangement and shape.*—Bright yellow-colored single flowers arranged in terminal compound umbels with about ten flowers per umbel. Flowers persistent. Flowers face mostly upright to slightly outwardly.

*Fragrance.*—None detected.

*Natural flowering season.*—Summer, typically June to September in The Netherlands.

*Postproduction longevity.*—Cut flowers are typically harvested when all flowers have developed fruits. Postproduction longevity of cut stems with fruits is about two weeks.

*Flower buds.— Length: About* 6 mm. Diameter: About 7.5 mm. Shape: Oblong. Color: 13C; towards the margin, 14A.

*Inflorescence size.*—Length: About 9 cm. Diameter: About 7 cm.

*Flowers.*—Diameter: About 2.8 cm. Depth (height): About 1 cm.

*Petals.*—Quantity/arrangement: Five in a single whorl. Length: About 1.2 cm. Width: About 8 mm. Shape: Broadly elliptic. Apex: Rounded to slightly retuse. Base: Attenuate. Margin: Entire. Texture, upper and lower surfaces: Glabrous, smooth. Color: When opening and fully opened, upper surface: 13A. When opening and fully opened, lower surface: 10A.

*Sepals.*—Quantity/arrangement: Five in a single whorl. Length: About 1 cm. Width: About 7.5 mm. Shape: Broadly cordate. Apex: Rounded. Base: Broadly attenuate. Margin: Entire. Texture, upper and lower surfaces: Glabrous, slightly rugose. Color: When opening, upper surface: 143C; towards the base, 2D; towards the margins, 46A. When opening, lower surface: Close to 147D. Fully opened, upper surface: 145B; towards the base, 137A; towards the margins, 46A. Fully opened, lower surface: 145D.

*Peduncles.*—Strength: Strong. Length: About 2.8 cm. Diameter: About 1.8 mm. Aspect: Erect to about 45° from vertical. Texture: Smooth, glabrous. Color: 144B overlain with 185A.

*Pedicels.*—Strength: Strong. Length: About 2 cm. Diameter: About 1.4 mm. Aspect: Erect to about 45° from the stem axis. Texture: Smooth, glabrous. Color: 144C overlain with 46A.

*Reproductive organs.*—Stamens: Quantity per flower: About 90. Filament color: 9A. Anther shape: Broadly ovate. Anther length: About 1 mm. Anther color: 17A. Pollen amount: Moderate. Pollen color: 13A. Pistils: Quantity per flower: Three. Pistil length: About 1.1 cm. Stigma shape: Globular. Stigma color: Close to 51A. Style length: About 6.1 mm. Style color: 3C. Ovary color: 1B.

*Fruits.*—Length: About 1.2 cm. Diameter: About 1 cm. Shape: Broadly ovate. Texture: Smooth; slightly ribbed. Color: 26C; at the apex, close to 187C.

*Seeds.*—Length: About 1.4 mm. Diameter: About 0.5 mm. Color: 200A.

Disease/pest resistance: Plants of the new *Hypericum* have not been noted to be resistant to pathogens and pests common to *Hypericum.*

Garden performance: Plants of the new *Hypericum* have exhibited moderate tolerance to rain and wind and have been observed to tolerate temperatures ranging from about −15° C. to about 35° C.

It is claimed:

1. A new and distinct *Hypericum* plant named 'Verpeacla' as illustrated and described.

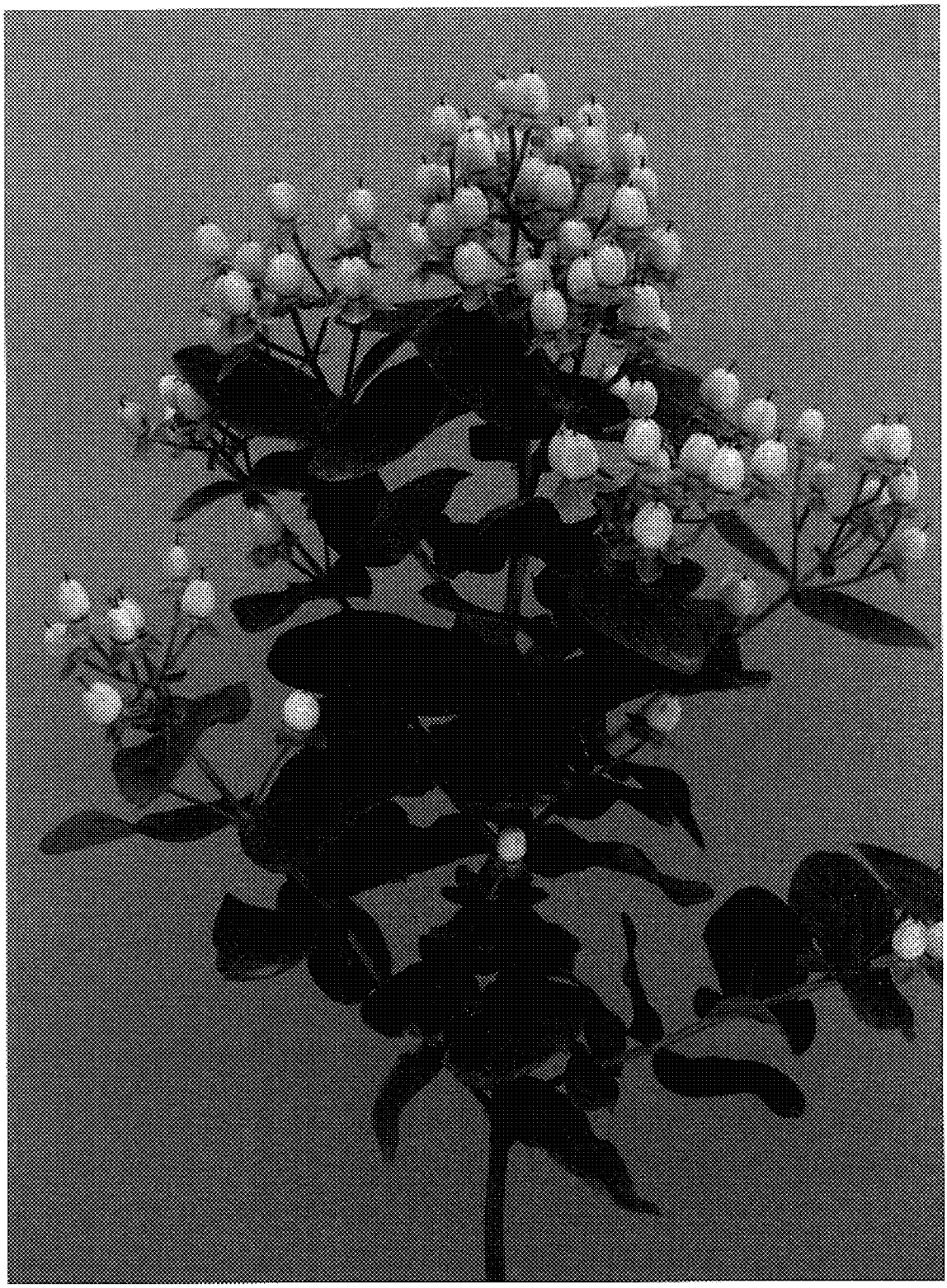

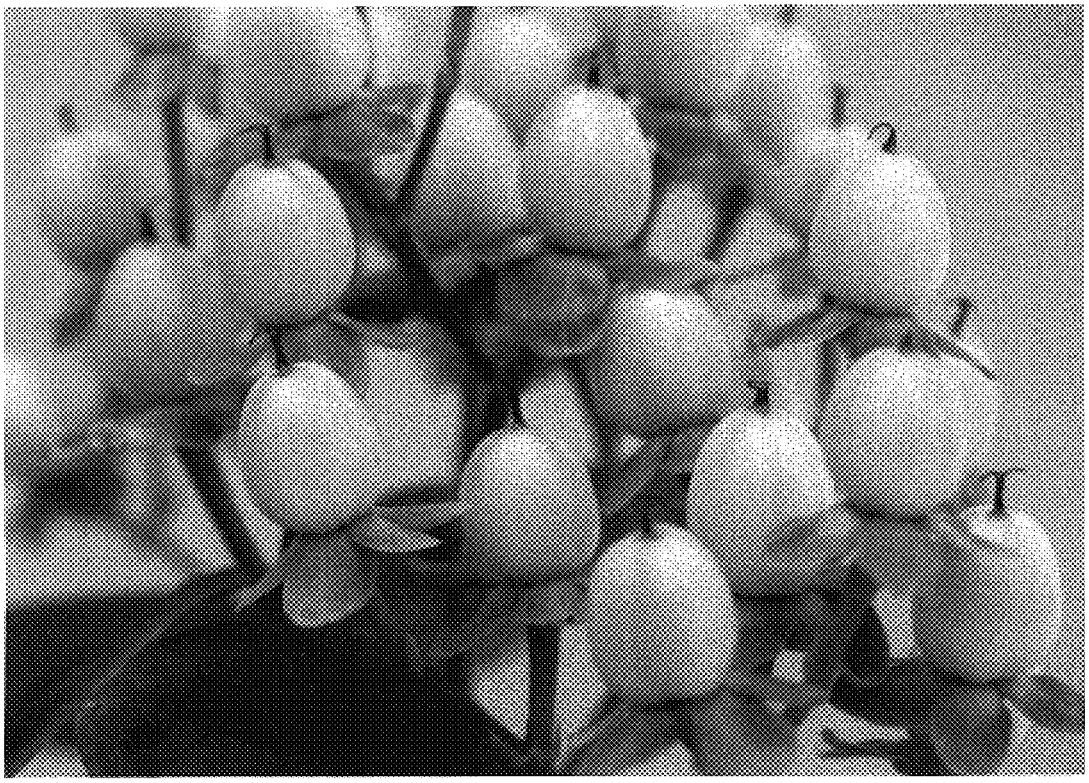
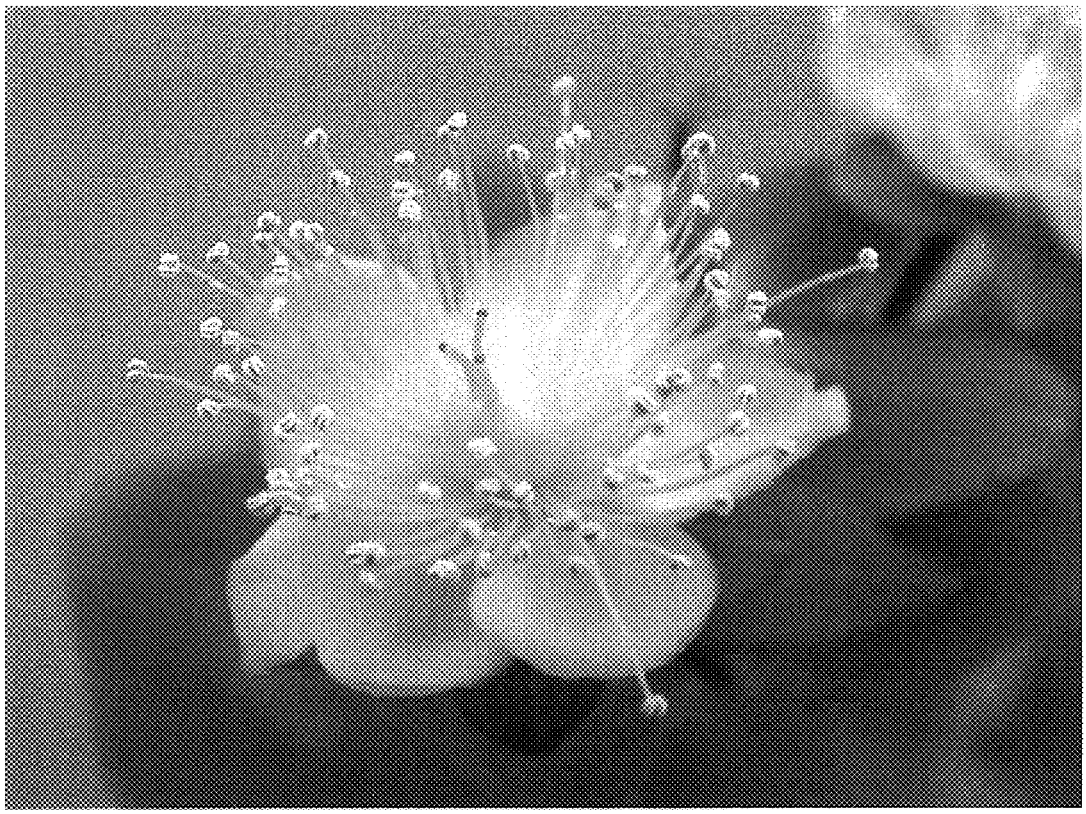

* * * * *